(12) United States Patent
Bullen et al.

(10) Patent No.: US 7,749,741 B2
(45) Date of Patent: Jul. 6, 2010

(54) TISSUE DISSOCIATION DEVICE

(75) Inventors: Lawrence Bullen, Centerburg, OH (US); Herbert S. Bresler, Columbus, OH (US); Daniel A. Kramer, Dublin, OH (US)

(73) Assignee: Battelle Memorial Institute, Columbus, OH (US)

( * ) Notice: Subject to any disclaimer, the term of this patent is extended or adjusted under 35 U.S.C. 154(b) by 696 days.

(21) Appl. No.: 10/572,495

(22) PCT Filed: Sep. 21, 2004

(86) PCT No.: PCT/US2004/030852

§ 371 (c)(1),
(2), (4) Date: Nov. 16, 2006

(87) PCT Pub. No.: WO2005/030936

PCT Pub. Date: Apr. 7, 2005

(65) Prior Publication Data

US 2007/0148756 A1     Jun. 28, 2007

Related U.S. Application Data

(60) Provisional application No. 60/504,772, filed on Sep. 22, 2003.

(51) Int. Cl.
*C12N 9/00* (2006.01)
*C12N 5/00* (2006.01)
*C12N 5/02* (2006.01)
*C12M 1/00* (2006.01)

(52) U.S. Cl. .................. 435/183; 435/283.1; 435/325; 435/366; 435/378; 435/379

(58) Field of Classification Search .................. None
See application file for complete search history.

(56) References Cited

U.S. PATENT DOCUMENTS 3,028,314 A * 4/1962 Means et al. ............... 435/43
3,938,784 A * 2/1976 Moreton ..................... 366/306
5,786,207 A * 7/1998 Katz et al. .................. 435/267

* cited by examiner

*Primary Examiner*—Christopher R Tate
*Assistant Examiner*—Aaron J Kosar
(74) *Attorney, Agent, or Firm*—MacMillan, Sobanski & Todd, LLC

(57) ABSTRACT

A tissue dissociation device (10) includes a container (12) having a sterile interior for holding the tissue to be dissociated and a liquid medium. The device (10) also includes a dissociation element (54), inside the container (12), for engaging the tissue to cause dissociation of the tissue. The device (10) also includes a resistive element (81), inside the container (12), for resisting movement of the tissue in response to the engagement by the dissociation element (54). Relative motion between and the resulting resistance provided by the resistive element (81) allows the dissociation element (54) to effectively dissociate the tissue. A powered tissue dissociation device includes a power source operatively connected to the dissociation element (54) for causing the dissociation element (54) to move into engagement with the tissue.

27 Claims, 3 Drawing Sheets

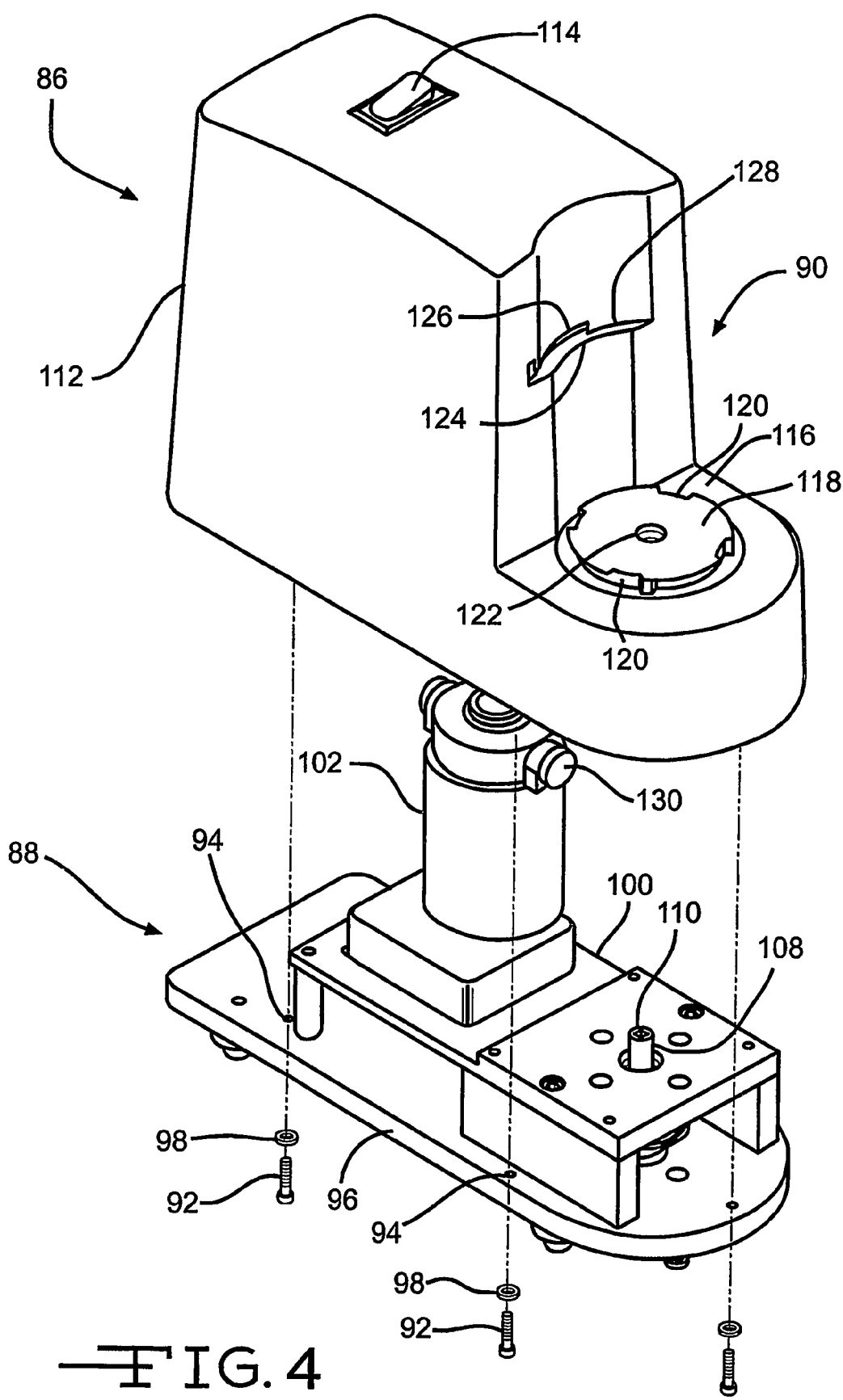

TISSUE DISSOCIATION DEVICE

CROSS-REFERENCE TO RELATED APPLICATION

This application claims the benefit of U.S. provisional application Ser. No. 60/504,772, filed Sep. 22, 2003.

BACKGROUND OF THE INVENTION

This invention relates in general to medical laboratory equipment, and in particular to a device for dissociating biological tissue.

In the fields of medicine and biological research, it is often necessary to dissociate a biological tissue into a single cell suspension. For example, an individualized cancer vaccine can be produced using a cancer patient's own tumor cells. An initial step of the vaccine process is to dissociate a tumor removed from the patient into a single cell suspension. A variety of physical and chemical dissociation methods are known, including cutting, scraping, mincing, or perfusing the tissue, and digestion with enzymes or nonenzymatic solutions. There is still a need for a tissue dissociation device for reducing tissue to a single cell suspension while maintaining cell viability and sterility of the sample, especially one that may work without the need for enzymes.

Various tissue dissociation devices are known in the art. For example, Hakki et al., "Nicotine Inhibition of Apoptosis in Murine Immune Cells", Experimental Biology and Medicine 226:947-953 (2001), discloses that spleen or thymus tissue was surgically removed and placed in a sterile plastic bag containing 10 ml of balanced salt solution. The bag was placed in a Stomacher 80 Lab Blender for 10 seconds to disrupt the tissue into a single cell suspension. The blender has paddles that beat against the bag to disrupt the tissue.

U.S. Pat. No. 5,786,207 to Katz et al., issued Jul. 28, 1998, discloses a device for dissociating tissue into a single cell suspension. The tissue is agitated with rotating dowels and filtered. The device maintains a sterile environment.

Various food blenders are also known in the art. For example, the Toastmaster Chopster Mini Food Chopper has a rotating shaft that holds a blade for chopping food into small pieces. This small food processor would not be suitable for reducing tissue to a single cell suspension while maintaining cell viability and sterility of the sample.

U.S. Pat. No. 3,938,784 to Moreton, issued Feb. 17, 1976, discloses a blender including a rotatable impeller having blades projecting radially outward. The impeller blades operate in cooperation with stationary blades mounted on the inner surface of the blending bowl that project radially inward. The blender is useful for mixing liquids and/or powders; it would not be suitable for reducing tissue to a single cell suspension while maintaining cell viability and sterility of the sample.

SUMMARY OF THE INVENTION

The present invention relates to a tissue dissociation device. The device includes a container having a sterile interior for holding the tissue to be dissociated and a liquid medium. The device also includes a movable dissociation element, inside the container, for engaging the tissue to cause dissociation of the tissue. The device also includes a resistive element, inside the container, for resisting movement of the tissue in response to the engagement by the dissociation element. The resistance provided by the resistive element allows the dissociation element to effectively dissociate the tissue.

The invention also relates to a powered tissue dissociation device. The device includes a power source operatively connected to the dissociation element for causing the dissociation element to move into engagement with the tissue. In a preferred embodiment, the power source is an independent power unit that mates with the device.

Relative motion between the dissociation element and resistive element is desired. In alternative embodiments useful in some applications, the power source may drive the container and resistive element, while the dissociation element is fixed in position, or is driven to rotate at a different speed in the same direction, or driven to rotate in an opposite rotation from that of the resistive element. Where multiple dissociation elements or resistive elements are provided, they may also be fixed in position, or driven in the same or opposite rotations and at the same or different speeds as other ones of the dissociation and resistive elements.

The invention also relates to a method of producing a cell suspension using the tissue dissociation device. The tissue and a liquid medium are inserted into the container of the device. The tissue is engaged with the moving dissociation element of the device. The resistive element of the device resists movement of the tissue in response to the engagement by the dissociation element. The resistance provided by the resistive element allows the dissociation element to effectively dissociate the tissue into a cell suspension.

Various advantages of this invention will become apparent to those skilled in the art from the following detailed description of the preferred embodiments, when read in light of the accompanying drawings.

BRIEF DESCRIPTION OF THE DRAWINGS

FIG. 4 is a perspective view of an independent power unit of the tissue dissociation device.

DETAILED DESCRIPTION OF THE INVENTION

Figure 1:
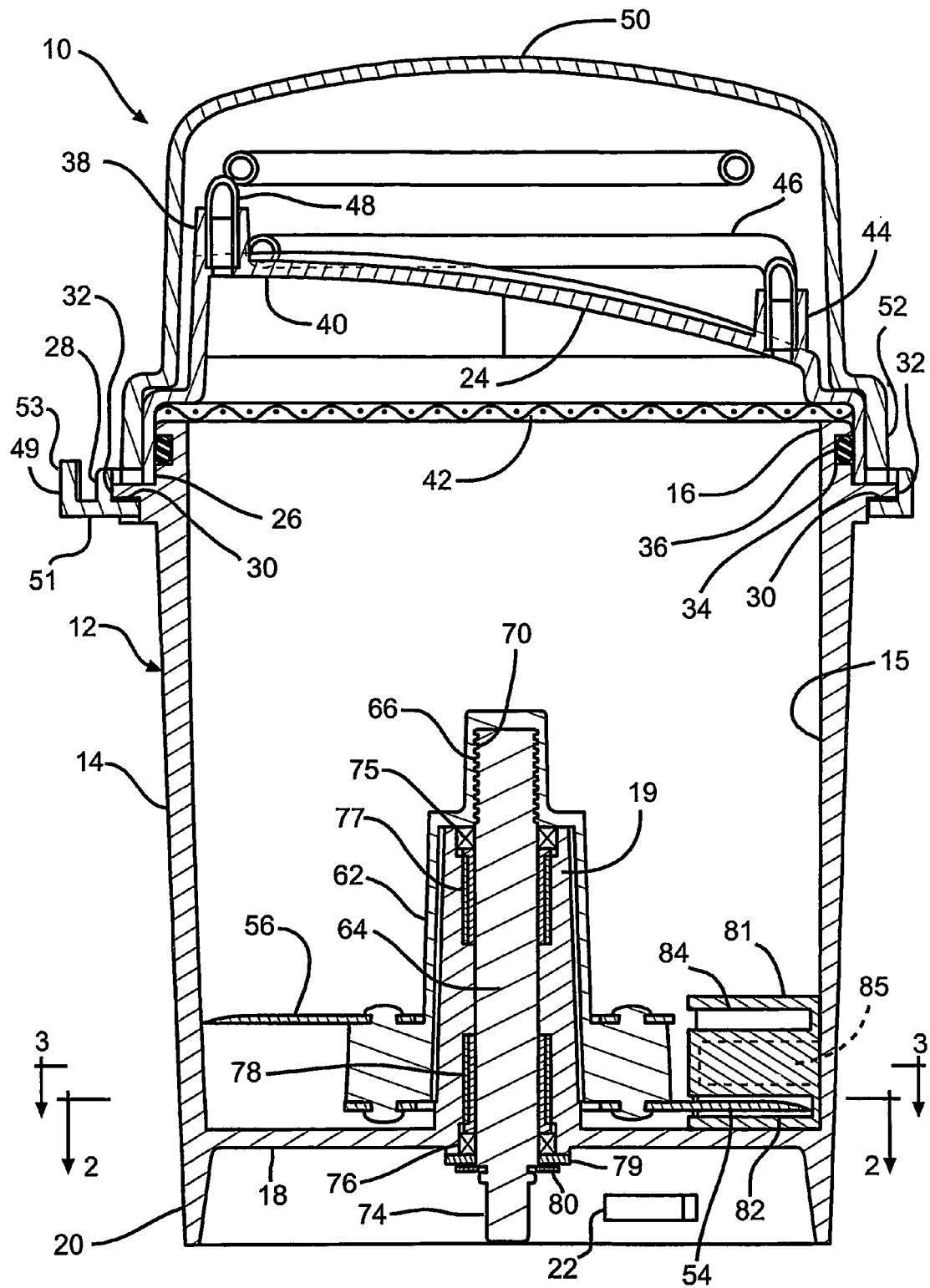
FIG. 1 is a side elevational view, in cross-section, of a tissue dissociation device according to the invention.

The present invention relates to a tissue dissociation device that is capable of dissociating biological tissue into a cell suspension. FIG. 1 illustrates a preferred embodiment of a tissue dissociation device 10 according to the invention. The device includes a container 12 for holding the tissue to be dissociated and a liquid medium. The container can have any suitable structure. In the illustrated embodiment, the container is cup-shaped, including a symmetrical outer wall 14 that is generally cylindrical in shape, an open upper end 16 and a closed lower end 18. The container has a sterile interior 15. In one embodiment, particularly useful with lung tumor cells, the container has a volume of from about 100 ml (about 6 cu inches) to about 1000 ml (about 60 cu inches). The size of the container may differ based on the type of tissue to be dissociated.

The container includes a tubular central hub 19 that extends upward inside the container from the lower end. The distance between the outer wall and the central hub is sufficient to allow the tissue to be inserted between them prior to dissociation.

Preferably, the container has a locking feature for locking it to an independent power source. Any suitable locking structure can be used. In the illustrated embodiment, the container includes a lower rim 20, and a pair of tabs 22 (one of which is shown) are formed inside the rim on opposite sides. The locking of the container to the power source using the tabs is described below.

The container can be made from any suitable material, such as plastic or metal. Preferably, the container is made from a rigid plastic that is clear to allow viewing the contents of the container during the dissociation and subsequent processes. The container is preferably compatible with air transport and other shipping methods, functioning as a dual use shipping and processing container.

The illustrated device 10 also includes a lid 24 connected to the upper end 16 of the container 12. The illustrated lid has an inner rim portion 26 and an outer rim portion 28. The lid and the container are connected together by any suitable connecting structure(s). In the illustrated embodiment, they are connected together by four equally spaced bayonet locks (two of which are shown) comprising sockets 30 in the outer rim portion 28 of the lid 24 and corresponding tabs 32 on the upper end 16 of the container 12. Not intending to be limited by these examples, other alternative connecting structures include threaded connections. The lid can be made from any suitable material, preferably a clear, rigid plastic.

Preferably, the lid is sealed to prevent liquid or gas from exiting or entering the container around the lid. Any suitable sealing structure can be used. In the illustrated embodiment, the container 12 has a ring-shaped groove 34 around its upper end 16 and an O-ring seal 36 is positioned in the groove. Alternatively, the ring-shaped groove and O-ring can be in the lid rather than in the end of the container (not shown). Regardless of the configuration, the inner rim portion 26 of the lid encircles the upper end 16 of the container 12 with the seal 36 therebetween, creating an air-tight seal between the container and the lid. In addition, a portion of the lid and container may further be threaded (not shown) so that the lid may be screwed onto the upper end of the container.

The illustrated lid 24 includes a fluid exchange port 38 that allows removal of the cell suspension from the container after dissociation. The fluid exchange port 38 also allows new liquid medium to be introduced into the container. Preferably, the lid has an asymmetric feature that facilitates complete removal of the contents of the container. In the embodiment shown, the lid is shaped to form a sump 40 that aids in the removal.

Preferably, the container includes a filter 42 associated with the fluid exchange port 38 for filtering the contents prior to removal. The filter 42 can be a screen or any other device for selective separation of materials based on size. The filter prevents the port from clogging and helps the downstream filtration process. In the embodiment shown, the filter 42 is mounted inside the lid 24, although it could alternatively be mounted inside the upper end 16 of the container 12.

The illustrated lid 24 also includes a gas exchange port 44 that allows air and other gases to move into and out of the container. Optionally, the tissue dissociation device can include a gas exchange filter (not shown) associated with the port, the filter having a porosity sufficiently low to allow gas to enter or exit the container while maintaining sterility of the interior of the container. The filtered gas exchange port facilitates inserting fluid into or draining fluid from the container while maintaining sterility of the container and its contents. The gas exchange filter can be located at any suitable position on the device, for example, attached to a gas exchange tubing lead 46 (described below). Other ways to accomplish a change in fluid volume, rather than venting, includes providing a flexible reservoir. The flexible reservoir may be, by way of example and not limitation, a balloon which expands to accept volume or contracts, or a flexible wall in a container, or a piston device to adjust volume in a container.

Although the illustrated container includes one fluid exchange port 38 and one gas exchange port 44, the container could have more or fewer than one of each. For example, the container could have two fluid exchange ports, one for introducing fluid into the container and the other for removing fluid from the container (e.g., for flushing the container). Further, although the illustrated fluid exchange port 38 and gas exchange port 44 are located in the lid 24 of the container 12, they could alternatively be located at other positions of the container. For example, the fluid exchange port 38 and the filter 42 could be located on the side of the container. This could facilitate a more continuous process.

Preferably, the interior of the container is sterilized before the tissue and the liquid medium are inserted, and the container is kept closed and sealed to maintain the sterility. By "closed" is meant either the container itself is closed, or the container is connected to other components as part of a functionally closed system. In the illustrated embodiment, both the gas exchange port 44 and the fluid exchange port 38 are structured to aseptically connect to Sterile Connect Device ("SCD") tubing: gas exchange tubing lead 46 and fluid exchange tubing lead 48, respectively, which lead to other vessels that are part of a closed system. The container is kept sealed with the above-described seal 36 between the container and the lid, and with another seal (described below) between the container and a drive shaft. SCD tubing is manufactured by Terumo Medical Corporation, 2101 Cottontail Lane, Somerset, N.J. 08873.

The lid 24 also may include an interlock feature 49 that assures correct installation of the container 12 with its lid attached on the power unit, as described below. Any suitable structure can be used for this purpose. In the illustrated embodiment, the interlock feature 49 is a projection formed on the perimeter of the lid. The interlock feature includes a short outwardly extending portion 51 and a short upwardly extending portion 53.

The illustrated device 10 also includes a cover 50 that fits over the lid 24 and the tubing leads 46 and 48, and that is removable prior to the dissociation process. The cover can be made from any suitable material, for example, an opaque, slightly flexible plastic. The cover can be connected to the lid by any suitable connecting structure(s). In the illustrated embodiment the cover has a rim 52 that fits closely around the inner rim portion 26 of the lid. The inner rim portion of the lid has ridges (not shown) that fit into corresponding grooves (not shown) in the rim of the cover, so that the cover can be connected to the lid by pushing it down onto the lid until the ridges snap into the grooves.

Figure 2:
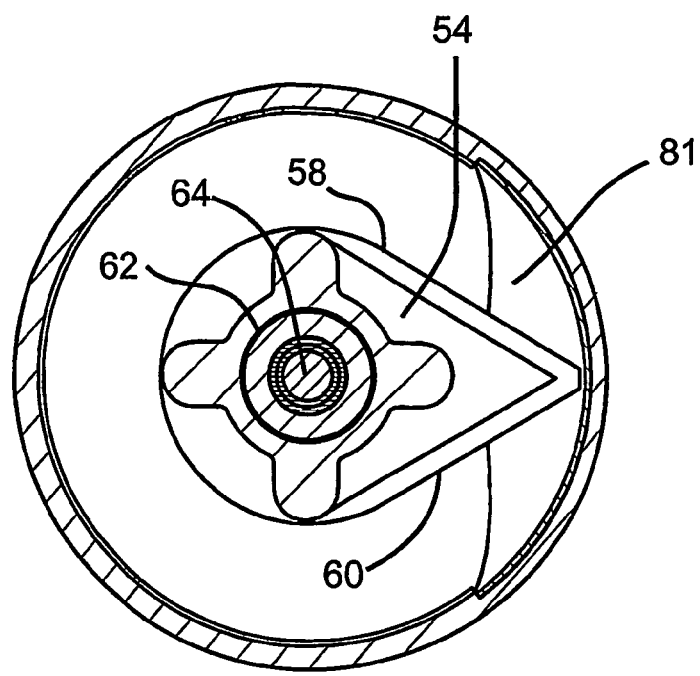
FIG. 2 is a cross-section of the tissue dissociation device taken along line 2-2 of FIG. 1.
Figure 3:
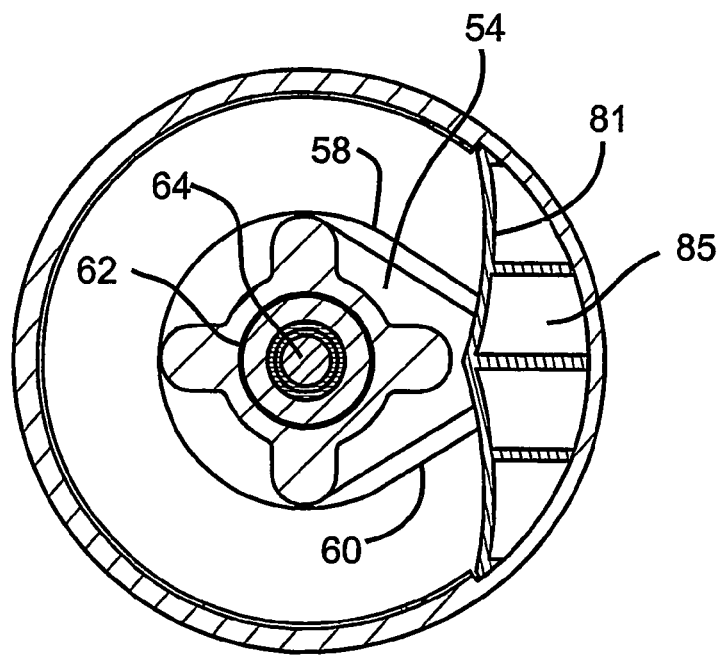
FIG. 3 is a cross-section of the tissue dissociation device taken-along line 3-3 of FIG. 1.

As shown in FIGS. 1-3, the tissue dissociation device 10 also includes a movable dissociation element, inside the container, for engaging the tissue to cause dissociation of the tissue. Any type of element(s) suitable for this purpose can be used. For example, the dissociation element could be a blade, a serrated member, a member having surface roughness, a rotating strand (e.g., a monofilament fiber), a member having 3-dimensional dissociation features (e.g., a length of barbed wire), or other members capable of tissue dissociation.

Preferably, the dissociation element comprises at least one blade 54. In the embodiment shown, the device also includes a second blade 56 as a dissociation element. The blades 54 and 56 can have any suitable structure for dissociating the tissue. As well, the blades 54 and 56 can also be multiple blades (not shown) in each location operating through slots 82 and 84, respectively. The illustrated blades are generally triangular plates having beveled cutting edges 58 and 60 along opposing sides of the blade. The blades can be made from any suitable material, for example, stainless steel. The dissociation element(s) can be movable in any direction(s) suitable for dissociating the tissue, for example, they can be disposed for rotational or oscillating movement.

The tissue dissociation device typically includes a drive structure for transferring motive power from a power source to the dissociation element(s). In the illustrated embodiment, the blades are mounted on a rotor 62, which is disposed about the central hub 19 of the container. The rotor can be made from any suitable material, for example, a rigid plastic or a metal. The rotor, in turn, is mounted for rotational movement on a centrally located drive shaft 64. The drive shaft and the rotor can be connected for rotation with any suitable structure (s). In the illustrated embodiment, the drive shaft and the rotor are rotatably connected by a textured outer surface 66 on the upper end of the drive shaft that engages a textured inner surface 70 inside the upper end of the rotor. The drive shaft can be made from any suitable material, for example, a metal such as stainless steel. The drive shaft extends through the lower end 18 of the container 12. The lower end 74 of the drive shaft has a square cross-section for attachment to an independent power unit (described below). Rotation of the drive shaft by the power unit causes the blades to rotate. Preferably, the direction of rotation of the drive shaft is reversible to free the dissociation element(s) from any obstructions that may occur during the dissociation process. The cutting edges 58 and 60 on opposing sides of the blades allow the blades to cut in both directions.

Because relative motion between the dissociation element and resistive element is desired, alternative embodiments are useful in some applications. Although not shown in the drawings, the power source may be configured to drive the device by driving the container 12, lid 24, cover 50 or resistive element 81 itself to move the resistive element, while the dissociation element is fixed in position. Or alternatively, the dissociation element and resistive element may move and rotate at different speeds or in opposite rotations from each other as may be desired in an application.

Preferably, the device 10 includes a sealing structure to prevent liquid or gas from exiting or entering the container around the drive shaft. In the illustrated embodiment, a pair of seals 75 and 76 are located between the drive shaft 64 and the central hub 19 of the container 12. Any suitable type of seals can be used, for example, rubber cup seals.

The device 10 may also include a mechanism to maintain the alignment of the drive shaft 64 and thereby the alignment of the rotor 62 and blades 54 and 56. In the illustrated embodiment, a pair of bushings 77 and 78 are located between the drive shaft 64 and the central hub 19 of the container 12. In addition to the bushings, a thrust washer 79 is used to maintain axial positioning and reduce friction. The thrust washer 79 is located between the lower end 18 of the container and a snap ring 80 which secures the drive shaft to the container.

The tissue dissociation device 10 also includes a resistive element, inside the container, for resisting movement of the tissue in response to the engagement by the dissociation element(s). The resistive element provides a resistance to the movement of the tissue that would otherwise occur in response to the engagement by the dissociation element. The resistance can result in any type of altered movement by the tissue; for example, the tissue can be held stationary by the resistive element, the tissue can be moved by the resistive element counter to the direction of movement of the dissociation element, or the tissue can be moved more slowly than would otherwise occur in the direction of movement of the dissociation element. The resistive element can be moving or stationary, so long as the relative motion between the resistive element and the dissociation element results in this resistance. Any type of element(s) suitable for this purpose can be used. For example, the resistive element can be a baffle, one or more blades that are either stationary or moving in a direction opposite that of the dissociation element(s), or a vertical metal fin with slots for dissociation elements in the form of blades to pass through.

In the illustrated embodiment, the resistive element is a stationary baffle 81 extending inward from the outer wall 14 of the container 12, and upward from the lower end 18 of the container. When viewed from the top (FIGS. 2 and 3), the baffle 81 has the shape of two intersecting circular segments. The baffle can be formed from any suitable material, for example, plastic or metal. In the embodiment shown, the baffle is a rigid plastic piece that is bonded with adhesive to the lower end and the outer wall of the container; however, it could also be formed integrally with the container.

The baffle 81 has first and second slots 82 and 84 extending radially almost to the outer wall 14 of the container 12. The first and second slots are positioned axially at the same level as the first and second blades 54 and 56, respectively. If the device had only one blade, the baffle could be made with a single slot, and if the device had more than two blades, the baffle could be made with more than two slots. As the blades rotate, they pass through the slots in the baffle. The baffle can optionally have hollow areas 85 to reduce the weight and cost of the baffle.

In an alternate embodiment, the baffle could be mounted in the center of the container, with the blade(s) spinning on a ring facing inward from the outer wall of the container. In another alternate embodiment, the baffle could be moving and the blade(s) stationary (in which case the baffle would be the dissociation element and the blade would be the resistive element).

The resistance provided by the resistive element allows the dissociation element to effectively dissociate the tissue. By "dissociate" is meant that the tissue is divided into single cells and/or small clumps of cells, or groups of cells of interest for a desired application. This can be accomplished in any suitable manner, such as by cutting, mincing, tearing, or shearing the tissue. The interaction between the dissociation element, the tissue, and the resistive element causes this dissociation. Without the resistive element, the dissociation element would be ineffective or less effective in dissociating the tissue. For example, a blade moving at a relatively low velocity (as discussed below) could merely push the tissue around the container instead of effectively cutting it; the baffle restraining the tissue allows the low velocity blade to effectively cut it.

A powered tissue dissociation device according to the invention includes a power source operatively connected to the dissociation element for causing the dissociation element to move into engagement with the tissue. In one embodiment (not shown), the power source is housed with the container of the tissue dissociation device. The power source would typically include a housing attached to or formed integrally with the container at any suitable location, for example, below the lower end of the container. A power source such as an electric motor would be mounted inside the housing. The motor would be connected by any suitable means for moving the dissociation element(s), for example, through a gear train or belt to the drive shaft in the container to cause rotation of the blades.

In a preferred embodiment, shown in FIG. 4, the tissue dissociation device includes an independent power unit 86. The illustrated power unit 86 includes a drive mechanism assembly 88, and a housing assembly 90 that fits over the drive mechanism assembly. The housing assembly is connected to the drive mechanism assembly in any suitable manner, for example, by a plurality of fasteners 92 (e.g., socket head cap screws) that extend through unthreaded holes 94 in the base 96 of the drive mechanism assembly and into corresponding threaded holes (not shown) in the bottom of the housing assembly. Optionally, washers 98 can be used with the fasteners.

The illustrated drive mechanism assembly 88 includes a frame 100 mounted on the base 96. Any suitable power source, such as a DC electric gear motor 102, is mounted on the rear portion of the frame. A power source is selected that will enable the desired movement of the dissociation element (s). In the illustrated embodiment, a motor is selected that will enable the desired rotational velocity of the blades of the tissue dissociation device.

The drive mechanism assembly also includes a rotatable output shaft 108 extending upward through a hole in the front portion of the frame. The motor is connected to provide rotational power to the output shaft by any suitable mechanism, for example, a toothed belt drive (not shown). The output shaft has a bore 10 in its upper end. The illustrated bore has a square cross-section to receive the square-shaped lower end 74 of the drive shaft 64 of the tissue dissociation device, thereby providing a driving connection between the output shaft and the drive shaft. However, the bore and the lower end of the drive shaft could have any other structure suitable for providing the driving connection, for example, a triangular or rectangular cross-section, or a splined structure.

The illustrated housing assembly 90 includes a housing body 112. The housing body, and the base and frame of the drive mechanism assembly, can be made from any suitable material(s), for example, a rigid plastic material or a metal. A forward/reverse/off switch 114 is mounted on top of the rear portion of the housing body. The housing also contains a master fused power switch (not shown), an AC to DC power supply (not shown) for the DC motor, and a thermal over temperature switch (not shown) to protect the power unit from overheating.

The power unit is constructed to interface with the container of the tissue dissociation device. Any suitable structure can be used for this purpose. In the illustrated embodiment, the front portion of the housing body has a recessed area 116. The recessed area is sized and shaped to receive the container 12 of the tissue dissociation device. A mounting structure 118 is formed on the bottom of the recessed area for mounting the container on the power unit. The mounting structure includes a locking structure for locking the container to the power unit. Any suitable locking structure can be used. In the illustrated embodiment, the mounting structure includes notches 120 into which the tabs 22 (FIG. 1) of the container are inserted. The container is then turned to lock the container to the mounting structure. The mounting structure has a hole 122 through which the output shaft 108 of the power unit extends for connection to the drive shaft 64 of the tissue dissociation device.

The power unit also includes an interlock feature 124 that prevents it from operating until the container with its lid attached is correctly installed on the power unit. Any suitable structure can be used for this purpose. In the illustrated embodiment, the interlock feature 124 includes a groove through the inner portion of the recessed area 116 of the housing body 112. The groove has a wide portion 126 and a narrow portion 128. When the container is installed on the power unit, the projection 49 formed on the perimeter of the lid 24 (FIG. 1) extends through the wide portion of the groove. When the container is turned to lock it to the power unit, the projection is turned to the narrow portion of the groove. The outwardly extending portion of the projection extends through the groove, and the upwardly extending portion of the projection is positioned inside the housing body adjacent to the groove, thereby locking the container to the power unit. When the upwardly extending portion of the projection is in this position, it pushes inward on an interlock switch (not shown) which is in series with the forward/reverse/off switch 114 on the top of the housing. The forward/reverse/off switch 114 is ineffective to start the motor until the interlock switch has been depressed by the projection on the lid.

The mounting structure 118 of the power unit assures that the cooperating interlock features of the power unit and the container are properly aligned with each other. Any suitable structure can be used for this purpose. In the illustrated embodiment, the mounting structure 118 has the general shape of a circular disk. The diameter of the disk is approximately the same as the inner diameter of the lower rim 20 of the container 12 (FIG. 1), so that the container fits firmly into place on the mounting structure. The mounting structure is located on the housing body in a position that places the interlock features in alignment with each other.

Preferably, the power source has overcurrent protection to protect the components of the powered tissue dissociation device in the event of a jam. The power source is preferably reversible to allow elimination of tissue jams in the tissue dissociation device. Optionally, the power unit can additionally include an anti-jam mechanism (not shown) to automatically issue an alarm or automatically reverse movement of the blade if a tissue jam occurs.

The power unit can also optionally include a timing mechanism (e.g., a time indicator or control) (not shown) to automatically stop the dissociation process at a predetermined time.

In a method of producing a cell suspension using the tissue dissociation device, the tissue to be dissociated, and a liquid medium, are inserted into the container of the device. The tissue dissociation device can be used to dissociate practically any type of biological tissue, including human, animal or plant tissue, and natural or engineered tissue. The tissue can be from a human or animal organ such the lungs, liver, kidneys pancreas, brain, or heart. By way of example and not limitation, in a particular embodiment, the tissue dissociation device is used to dissociate human lung tumor cells. The insertion of the tissue into the container can be done at any suitable location. In some applications, the insertion of the tissue is done in an operating room under sterile conditions.

The liquid medium inserted into the container with the tissue allows the effective dissociation of the tissue into a cell suspension. Operating the tissue dissociation device without the liquid medium would not effectively dissociate the tissue. This contrasts with devices such as food choppers that work for their intended purpose without a liquid medium. The liquid medium can be practically any type of liquid that is compatible with the tissue and the dissociation process. Typically, the liquid medium is water-based and contains enough salt to prevent the cells from disrupting due to osmotic pressure differential. Some examples of a suitable liquid medium include saline solution, buffered saline solution, ringer's lactate solution, cell culture medium, Plasmalyte, and other fluids known in the art. Antibiotics, stabilizers, proteins, and other additives can be included in the liquid medium.

The liquid medium can be prepackaged with the container or it can be added later. The amount of liquid medium used can be determined for a particular application. The ratio of liquid medium to tissue may have an effect in maintaining the viability of the cells produced by the dissociation process. For example, the tissue and the liquid medium may be inserted into the container in a weight ratio that maintains the viability of a substantial portion of the cells. The amount of liquid medium used may also affect the dissociation. For example, if the appropriate amount of liquid medium is used, the tissue stays down in the container in the path of the rotating blades, but if too much liquid medium is used, the tissue may float on top of the liquid medium and above the blades. The container can be provided with a fill line to indicate the appropriate amount of liquid medium.

After the tissue and the liquid medium have been added to the container, the tissue is engaged with the moving dissociation element(s), such as the rotating blades described above. The resistance to tissue movement provided by the resistive element(s) allows the dissociation element(s) to effectively dissociate the tissue into a cell suspension. The cooperation of the dissociation element(s) and the resistive element(s) allows the dissociation element(s) to move in a manner that maintains the viability of the cells produced by the dissociation method, while still effectively dissociating the tissue into single cells and/or clumps of cells. The yield of viable cells and viable materials by the method will depend on source material and intended use. The device can deliver high yield, and high viability from a healthy tissue where such are desired.

For example, the cooperative action on the tissue by the dissociation element(s) and the resistive element(s) can allow the dissociation element(s) to maintain cell viability by moving at a relatively low speed while still effectively dissociating the tissue. Typically, the dissociation element moves at a dissociation speed within a range at which a substantial portion (greater than about 50%) of the cells produced by the method are both dissociated and viable. In some applications up to 95% of the cells produced in accordance with the present invention were viable. In some embodiments, the dissociation element has a portion that moves the most rapidly during the dissociation (e.g., the tip of a rotating blade), and this portion moves at a velocity of from about 100 mm/second (about 250 inches/minute) to about 200 mm/second (about 500 inches/minute). For example, if the dissociation element is a rotating blade, the blade may have a length of from about 25 mm (about 1 inch) to about 50 mm (about 2 inches) and rotate at a velocity of from about 50 rpm's to about 100 rpm's. The dissociation speed will depend on the particular application and the structure of the dissociation device, as well as the desired level of cell viability, amount of dissociation, and time of the dissociation process.

The motion of the dissociation element(s) is usually sufficient to draw the tissue into the path of the dissociation element. In other words, the dissociation element causes enough agitation so that the tissue is drawn down into the liquid medium and into the path of the dissociation element, instead of staying on top of the liquid medium.

The dissociation of tissue using the tissue dissociation device of the invention is typically quicker than conventional dissociation methods. For example, the dissociation of tumor tissue may take between about 10 and 15 minutes using the tissue dissociation device, whereas dissociation of the tissue by cutting with scalpels and then enzymatic digestion may take 2 hours or more. Usually, the dissociation using the tissue dissociation device is conducted for a time not greater than about 15 minutes.

The tissue dissociation device can be used for many different applications, and it can be used in a variety of ways. In a typical method of dissociating tissue using the device, a tissue sample is placed into the container of the device along with a shipping medium (usually a cell culture medium containing an antibiotic). The container is then transferred, preferably in a refrigerated state for tumor tissues, although other tissues, such as plant tissues in a proper medium need not be refrigerated, to a processing center. The shipping medium is drained off, aseptically, prior to processing. Processing fluid (a liquid medium, typically a buffered saline solution) is added aseptically to the container. Then the container is attached to an independent power unit. The power unit is turned on, and the tissue dissociation device is operated to dissociate the tissue into a cell suspension. The cell suspension is then transferred aseptically to a filtration process. After filtration, the cell suspension is transferred aseptically to a sterile vessel for further processing.

In one particular application, the tissue dissociation device is used as part of a process for producing an individualized cancer vaccine using a cancer patient's own tumor cells. A sample of tumor tissue is removed from the patient by a physician in an operating room. The tumor tissue is placed directly into the container of the tissue dissociation device for transporting the tissue to a vaccine processing location. The tumor tissue is submerged in a shipping medium inside the container to help maintain the viability of the tissue during transport. The container remains closed after the operating room to maintain the sterility of the tumor tissue. At the vaccine processing location, the container of the tissue dissociation device is installed on its power unit for dissociating the tumor tissue into a cell suspension. Optionally, an enzyme can be used in conjunction with the tissue dissociation device to digest the tissue and thereby aid in the dissociation. Any suitable enzyme can be used, such as collagenase. The tissue dissociation device can serve as the digestion chamber by introducing the enzyme through SCD tubing into the fluid exchange port of the container. This speeds up the process and helps to maintain the sterility of the tissue in a closed system.

The tissue dissociation device was used in a series of 20 trials to recover cells from various types of human tumor tissue. The results are summarized in the following table:

|  | Cells recovered per gram of tissue | Percent viability |
| --- | --- | --- |
| High | $2.9 \times 10^9$ | 95% |
| Low | $6.2 \times 10^5$ | 14% |
| Mean | $2.6 \times 10^8$ | 70% |
| Standard Deviation | $6.4 \times 10^8$ | 19 |

In accordance with the provisions of the patent statutes, the principle and mode of operation of this invention have been explained and illustrated in its preferred embodiments. However, it must be understood that this invention may be practiced otherwise than as specifically explained and illustrated without departing from its spirit or scope.

What is claimed is:

1. A tissue dissociation device comprising:
   a container;
   a dissociation element comprising at least one blade having beveled cutting edges on opposing sides of the blade, the dissociation element positioned inside the container and suitable for engaging tissue to cause dissociation of the tissue; and
   a resistive element comprising at least one baffle positioned inside the container to resist movement of the tissue and capable of being engaged by the at least one blade, the at least one baffle having at least one slot through which the at least one blade passes;

wherein at least one of the dissociation element and resistive element are movable relative to the other such that the resistance provided by the resistive element allows the dissociation element to effectively dissociate the tissue.

2. A device according to claim 1 wherein the at least one blade is disposed for rotational movement inside the container.

3. A device according to claim 1, wherein the at least one baffle having at least one slot comprises at least one of said baffle having at least two of said slots, wherein the dissociation element comprises at least two blades, and wherein the blades are positioned so that each blade passes through a separate slot selected from each of the at least two slots.

4. A device according to claim 1 wherein the device further comprises at least one power source for driving at least one of the dissociation element and resistive element in motion relative to one another, to engage the tissue, wherein the motion is a directional rotational motion which is driven by the power source, and wherein the direction driven by the power source is reversible.

5. A device according to claim 1 wherein the device further comprises a rotatable drive shaft for driving the dissociation element to engage the tissue, the container further comprises a seal, and the drive shaft extends through the seal to prevent liquid or gas from exiting or entering the container around the drive shaft.

6. A device according to claim 1 wherein the container further comprises a lid, and the lid is sealed to prevent liquid or gas from exiting or entering the container around the lid.

7. A device according to claim 1 wherein the container further comprises a port for removing contents from the container, and a filter associated with the port for filtering the contents prior to removal thereof.

8. A device according to claim 1 wherein the container further comprises a lid having a port for removing the contents from the container, and the lid has an asymmetric feature that facilitates complete removal of the contents.

9. A device according to claim 1 wherein the container further comprises a locking feature for locking the container in a fixed position against rotational forces.

10. A device according to claim 1 wherein the container further comprises an outer wall and a central hub, and the distance between the outer wall and the central hub is sufficient to allow the tissue to be inserted therebetween prior to dissociation.

11. A device according to claim 1 wherein the container further comprises a gas exchange port, and a filter associated with the gas exchange port, the filter having a porosity sufficiently low to allow gas to enter or exit the container while maintaining the sterility of the interior of the container.

12. A device according to claim 1 wherein the container further comprises a gas exchange port and a fluid exchange port, and both ports are structured to make an aseptic connection.

13. A device according to claim 1 wherein the interior of the device is sterile.

14. A device according to claim 1 wherein the device further comprises at least one power source operatively connected to drive at least one of the dissociation element and the resistive element in motion relative to one another to engage the tissue.

15. A device according to claim 14 wherein the at least one power source is an independent power unit comprising a power unit body structured to receive the container, and at least one motor associated with the power unit body, and the device further comprises a drive structure for transferring motive power directly or indirectly from at least one of the motors to at least one of the dissociation element and the resistive element.

16. A device according to claim 15 wherein the device further comprises a lid for the container and a power interlock mechanism, wherein the power interlock mechanism prevents the power unit from operating until the container and the lid are correctly installed on the power unit.

17. A device according to claim 15 wherein the power unit further comprises an anti jam mechanism to automatically issue an alarm or automatically reverse movement of the dissociation element relative to the resistive element if a tissue jam occurs during dissociation of the tissue.

18. A device according to claim 15 wherein the power source further comprises a timing mechanism to automatically stop dissociation of the tissue at a predetermined time.

19. A device according to claim 1 wherein the dissociation element and the resistive element rotate in the same direction at different speeds.

20. A device according to claim 1 wherein the at least one blade is disposed for oscillating movement inside the container.

21. A device according to claim 4 wherein the at least one blade is disposed for oscillating movement inside the container.

22. A device according to claim 4 wherein the at least one power source is an independent power unit comprising a power unit body structured to receive the container, and at least one motor associated with the power unit body, and the device further comprises a drive structure for transferring motive power directly or indirectly from the at least one motor to at least one of the dissociation element and the resistive element.

23. A device according to claim 22 wherein the device further comprises a lid for the container and a power interlock mechanism, wherein the power interlock mechanism prevents the power unit from operating until the container and the lid are correctly installed on the power unit.

24. A device according to claim 22 wherein the power unit further comprises an anti-jam mechanism to automatically issue an alarm or automatically reverse movement of the dissociation element relative to the resistive element if a tissue jam occurs during dissociation of the tissue.

25. A device according to claim 22 wherein the power source further comprises a timing mechanism to automatically stop dissociation of the tissue at a predetermined time.

26. A device according to claim 4 wherein the power source moves the most rapidly moving portion of the blade at a velocity relative to the baffle within a range of from about 100 mm/second to about 200 mm/second.

27. A device according to claim 4 wherein the blade has a length within a range of from about 25 mm to about 50 mm, and the power source moves the blade in rotation relative to the baffle at a velocity within a range of from about 50 rpm to about 100 rpm.

* * * * *